Nov. 2, 1965 W. S. HAHN Plant Pat. 2,568
AZALEA PLANT
Filed June 2, 1964
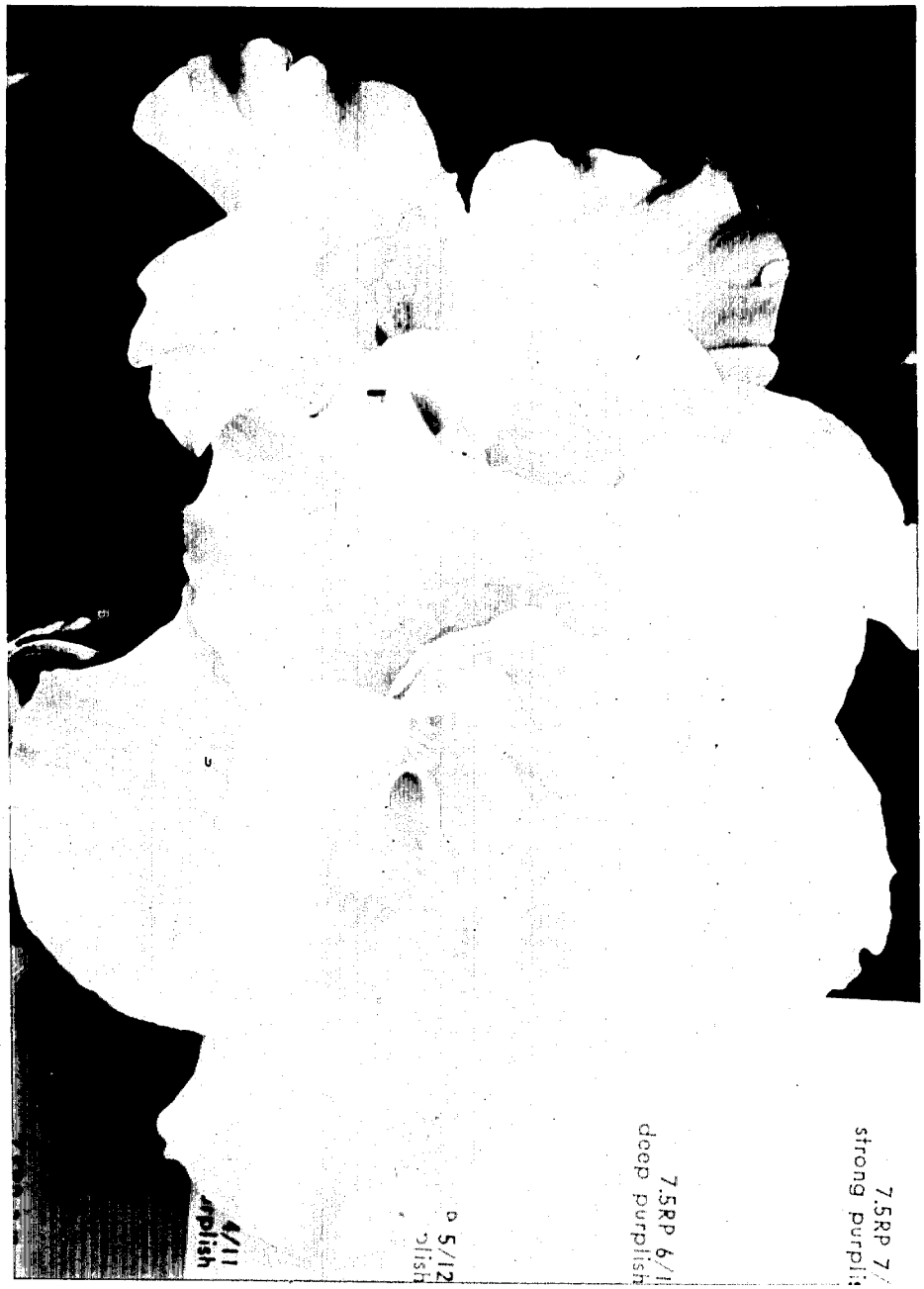
INVENTOR
Walter S. Hahn
By Orville M. Kile
Plant Patent Agt.

United States Patent Office

Plant Pat. 2,568
Patented Nov. 2, 1965

2,568
AZALEA PLANT

Walter S. Hahn, Millvale Post Office, Pittsburgh, Pa.

Filed June 2, 1964, Ser. No. 372,132
1 Claim. (Cl. Plt.—57)

My present discovery is a new variety of *Azalea indica* and was discovered by me as a bud sport or mutation of the *indica* variety Nancy Kay (unpatented) in the course of my constant search and observation in my extensive greenhouses in the suburbs of Pittsburgh for new and promising cultivars. I have been reproducing asexually this cultivar by means of vegetative terminal cuttings for a number of years and now have on hand a considerable number of plants that have bloomed and shown that their distinguishing characteristics reproduce faithfully.

My new cultivar is distinguished from other *Azalea indica* cultivars chiefly by the coloration of its flowers. The parent variety's blossoms lack the depth and intensity of those of the claimed variety, and fade under artificial light. My new variety grows rapidly and is easily propagated from cuttings, which mature and survive for many years as "own-root" plants, thereby eliminating the necessity of grafting onto a hardier rootstock in order to provide a satisfactory root system.

The accompanying illustration shows in full color a typical blossom of this new cultivar, insofar as color photography is able to reproduce it, but certain qualities to be described below, both of the flower and the plant, cannot be shown in a photograph or painting. Another outstanding characteristic of this new variety is that through proper manipulation of light and temperature the plant can be flowered at any desired time of year.

In the following detailed description, color plate designations are those of the Nickerson Color Tan.

*The plant*

In appearance the plant or shrub of this new variety, when not in bloom, is typical of that of the *Azalea indica*. The type of foliage, its overall shape and most habits of growth are those of *Azalea indica*. It does however grow from terminal cuttings with unusual rapidity and vigor. It produces a compact well-budded specimen some 8 inches tall and 8 inches across the top within a period of twelve months from the time the cutting is rooted, thus producing salable blooming plants in a relatively short time.

Unlike many varieties of *Azalea indica* it is not necessary to graft this new variety on understock in order to produce plants that develop a satisfactory root system and live a full life. The plant is a prolific bloomer, bearing an abundance of large, well-spaced individual flowers.

*The flower*

The flowers average from 3 to 3½ inches across. They are fully double and possess the typical "hose in hose" appearance characteristic of many *Azalea indica* cultivars.

Color: The overall color of the corolla as determined by the Nickerson Color Fan ranges from Deep Purplish Pink 7.5RP 6/12 to Strong Purplish Pink RP7.5 6/12. This coloration is uniform throughout the corolla except that it is interrupted principally on the dorsal portion of the petals by small dots and thin striations of Strong Purplish Red 10RP 4/12 on the throats of the corollas. A remarkable observation of the coloration of this new cultivar is that the same color is retained whether viewed in daylight, under artificial incandescent or fluorescent light. The dominant color is retained by the flowers from bud stage through maturity without fading or thinning.

Texture: The flowers have a velvety lustrous quality and are of thick substance which is retained through the life of the flower. There is very little if any loss of substance.

Tenacity: The flowers remain on the plant for a long period of time, they do not shatter from the plant, being tenaciously held until they collapse from old age.

Having thus disclosed my discovery, I claim:

The new and distinct variety of *Azalea indica* characterized particularly by the deep purplish pink coloration of its large, fully double flowers, that it can be made to flower at any time of year desired, its ready propagation from cuttings with ability to sustain itself for many years on its own root system, and exceedingly rapid growth from cuttings, thus producing large salable plants in a shorter time than many other varieties of *Azalea indica*.

No references cited.

ABRAHAM G. STONE, *Primary Examiner.*